United States Patent
Diana

Patent Number: 5,242,924
Date of Patent: Sep. 7, 1993

[54] TETRAZOLYL-(PHENOXY AND PHENOXYALKYL)-PIPERIDINYLPYRIDAZINES AS ANTIVIRAL AGENTS

[75] Inventor: Guy D. Diana, Stephentown, N.Y.

[73] Assignee: Sterling Winthrop Inc., New York, N.Y.

[21] Appl. No.: 909,403

[22] Filed: Jul. 2, 1992

[51] Int. Cl.$^5$ .................. A61K 31/50; C07D 401/04
[52] U.S. Cl. .................... 514/252; 544/238
[58] Field of Search .................... 544/238; 514/252

[56] References Cited

FOREIGN PATENT DOCUMENTS 320032 11/1986 European Pat. Off. .
435381 7/1991 European Pat. Off. .

*Primary Examiner*—Cecilia Tsang
*Attorney, Agent, or Firm*—Paul E. Dupont

[57] ABSTRACT

Compounds of the formula

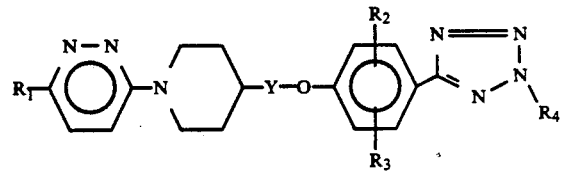

wherein:
  Y is a bond, or $C_1$–$C_6$ alkylene;
  $R_1$ is hydrogen or $C_1$–$C_3$ lower-alkyl;
  $R_2$ and $R_3$ are each independently hydrogen, $C_1$–$C_3$ lower-alkyl or halogen;
  $R_4$ is hydrogen or $C_1$–$C_3$ lower-alkyl;

or pharmaceutically acceptable acid addition salts thereof are useful as antiviral agents, particularly against picornaviruses.

30 Claims, No Drawings

TETRAZOLYL-(PHENOXY AND PHENOXYALKYL)-PIPERIDINYLPYRIDAZINES AS ANTIVIRAL AGENTS

BACKGROUND OF THE INVENTION a) Field of the Invention

This invention relates to novel tetrazolyl-(phenoxy and phenoxyalkyl)-1-piperidinylpyridazines and to compositions and methods of use thereof as antiviral agents.

b) Information Disclosure Statement

European Patent Application No. 320032, published Nov. 17, 1986, discloses compounds having the formula

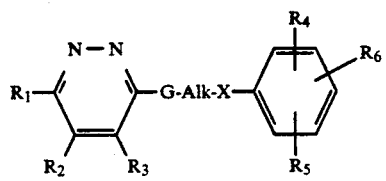

wherein:

$R_1$ is hydrogen, $C_{1-6}$alkyl, halo, hydroxy, mercapto, trifluoromethyl, amino, mono or di($C_{1-6}$alkyl)amino, cyano, $C_{1-6}$alkyloxy, aryloxy, aryl$C_{1-6}$alkyloxy, $C_{1-6}$alkylthio, arylthio, $C_{1-6}$alkylsulfinyl, $C_{1-6}$alkylsulfonyl, arylsulfinyl, arylsulfonyl, $C_{1-6}$alkoxycarbonyl, $C_{1-6}$alkyl-carbonyl, or aryl;

$R_2$ and $R_3$ each independently are hydrogen or $C_{1-6}$alkyl, or $R_2$ and $R_3$ combined may form a bivalent radical of formula —CH=CH—CH=CH—

Alk is an alkane chain 0-6 carbons long

G is a bivalent radical of formula

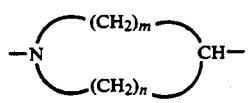

n is 2-3 carbons
m is 2-3 carbons

X is O, S, $NR_8$ or a direct bond; said $R_8$ being hydrogen or $C_{1-6}$alkyl.

$R_4$, $R_5$ and $R_6$ are independently H, halo, $C_{1-6}$alkyl, amino, cyano or nitro. The compounds are stated to have antiviral activity.

European Patent Application 435381, published Jul. 3, 1991, discloses pyridazinamines of formula

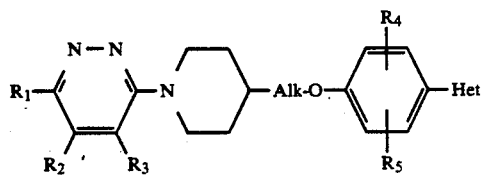

wherein $R_1$ is hydrogen, $C_{1-4}$alkyl, halo, hydroxy, trifluoromethyl, cyano, $C_{1-4}$alkoxy, $C_{1-4}$alkylthio, $C_{1-4}$alkylsulfinyl, $C_{1-4}$alkylsulfonyl, $C_{1-4}$alkyloxycarbonyl, $C_{1-4}$alkylcarbonyl or aryl;

$R_2$ and $R_3$ are hydrogen or $C_{1-4}$alkyl;

Alk is $C_{1-4}$alkanediyl;

$R_4$ and $R_5$ are hydrogen, $C_{1-4}$alkyl or halo; and

Het is

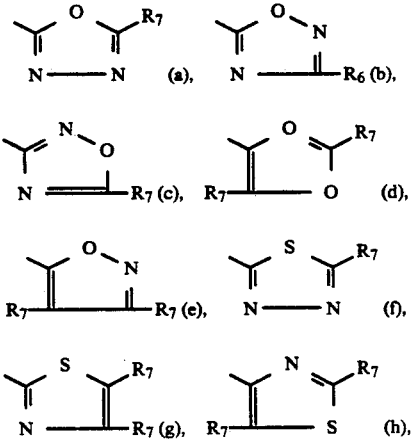

wherein $R_6$ is hydrogen, $C_{1-6}$alkyl; hydroxy$C_{1-6}$alkyl; $C_{3-6}$cycloalkyl; aryl; aryl$C_{1-4}$alkyl; $C_{1-4}$alkyloxy$C_{1-4}$alkyl; $C_{3-6}$cycloalkyl$C_{1-4}$alkyl; trifluoromethyl or amino;

each $R_7$ independently is hydrogen; $C_{1-6}$alkyl; $C_{3-6}$cycloalkyl; aryl; aryl$C_{1-4}$alkyl; $C_{1-4}$alkyloxy$C_{1-4}$alkyl; $C_{3-6}$cycloalkyl$C_{1-4}$alkyl or trifluoromethyl; and each aryl independently is phenyl or phenyl substituted with 1 or 2 substituents each independently selected from halo, $C_{1-4}$alkyl, trifluoromethyl, $C_{1-4}$alkyloxy or hydroxy. The compounds are stated to have antiviral activity.

SUMMARY OF THE INVENTION

It has now been found that phenoxy- or phenoxyalkylpiperidinylpyridazines wherein the phenoxy group is substituted with a tetrazolyl or substituted tetrazolyl group are effective antiviral agents.

Accordingly the present invention relates to compounds of the formula:

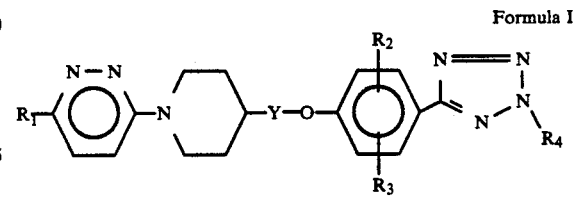

Formula I wherein

Y is a bond, or $C_1$-$C_6$ alkylene;

$R_1$ is hydrogen or $C_1$-$C_3$ lower-alkyl;

$R_2$ is hydrogen, $C_1$-$C_3$ lower-alkyl or halogen;

$R_3$ is hydrogen, $C_1$-$C_3$ lower-alkyl or halogen;

$R_4$ is hydrogen, or $C_1$-$C_3$ lower-alkyl;

or pharmaceutically acceptable acid addition salts thereof.

A preferred class of compounds within the scope of Formula I are those of the formula II

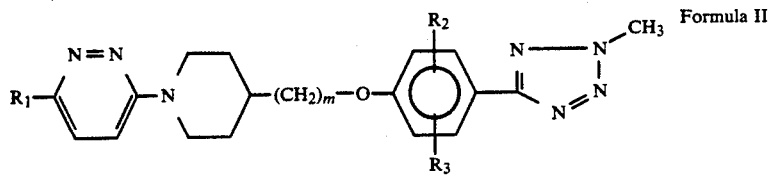

Formula II wherein:
 $R_1$ is hydrogen or $C_1$-$C_3$ lower-alkyl;
 $R_2$ and $R_3$ are each independently hydrogen or $C_1$-$C_3$ lower-alkyl or fluorine;
 m is 0–2;
or pharmaceutically acceptable acid addition salts thereof.

The invention also relates to compositions for combating viruses comprising an antivirally effective amount of a compound of Formula I with a suitable carrier or diluent, and to methods of combating viruses therewith, including the systemic treatment of viral infections in a mammalian host.

DETAILED DESCRIPTION INCLUSIVE OF PREFERRED EMBODIMENTS

As used herein the term halogen means fluorine, chlorine, bromine and iodine. The term $C_1$-$C_6$ alkylene refers to divalent straight or branched hydrocarbon radicals having from one to six carbon atoms and thus includes methylene, 1,2-ethylene, 1,3-propylene, 1,4-butylene, 1,6-hexylene, 1-methyl-1,4-butylene and the like. DEAD refers to diethyl azodicarboxylate. DIPEA refers to diisopropylethylamine. THF, NMP and DMF are tetrahydrofuran, N-methylpyrrolidine and N,N-dimethylformamide, respectively.

Compounds of formula I are made by two general procedures outlined below. In the formulas below, unless specifically defined otherwise, $R_1$, $R_2$, $R_3$, $R_4$ and Y, have the meanings given above in formula I.

METHOD A

The compounds of formula I are prepared by reacting phenol

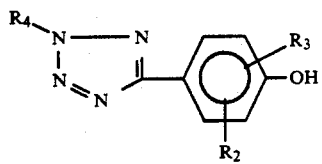

III with a suitable piperidine IV

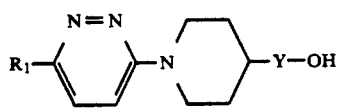

IV in the presence of triphenylphosphine and diethyl azodicarboxylate (DEAD) in a noninteracting solvent at a temperature in the range of about −50° C. to 48° C. preferably at about 0° C.

PREPARATION OF INTERMEDIATES

The tetrazolyl phenol III is prepared by reacting an appropriate $R_2$-$R_3$-4-cyanophenol preferably protected, e.g. as the benzyl ether, with sodium azide in a noninteracting solvent, e.g. DMF preferably under an inert atmosphere at a temperature between 100° and 150° C. for about 15-25 hours. The resulting tetrazole which can exist in two tautomeric forms (Va, Vb, Bz=benzyl):

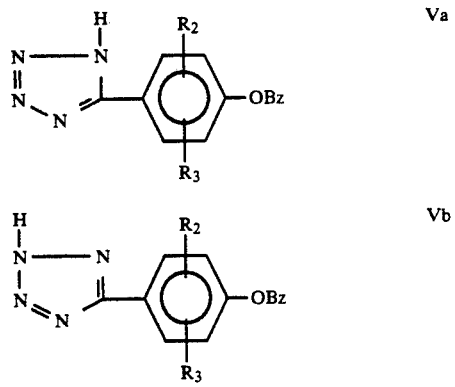

is then reacted with an alkylating agent, e.g. an alkyl halide, $R_4X$, preferably under inert atmosphere. Alkylation can occur at either available nitrogen atom and the desired isomer can be separated by conventional means, e.g. fractional crystallization or chromatography. Deprotection, e.g. reacting the benzyl ether with a strong acid such as HCL in acetic acid, affords III.

Intermediate IV is prepared from 4-hydroxypiperidine or 4-(hydroxyalkyl)piperidine and the substituted or unsubstituted halopyridazine VI (X is halogen, preferably chloro or bromo):

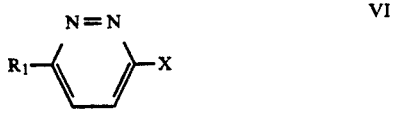

VI by reacting them in the presence of diisopropylethylamine (DIPEA) in a noninteracting solvent (e.g. THF, NMP, DMF), at a temperature range from about 25° to 110° C. preferably under an inert atmosphere.

The starting materials $R_2$-$R_3$-4-cyanophenol, 4-hydroxypiperidine, 4-(hydroxyalkyl)piperidine and 3-halo-6-$R_1$-pyridazine (VI) belong to known classes of compounds and are available commercially or can be prepared by methods well known in the art.

METHOD B

Compounds of formula I can also be prepared by reacting halopyridazine VI with the piperidine VII

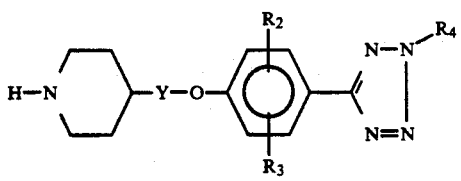

VII in the presence of DIPEA (diisopropylethylamine) and a noninteracting solvent as described above for the preparation of intermediate IV.

Intermediate VII is prepared by reacting phenol III with a 4-hydroxypiperidine or 4-(hydroxyalkyl)piperidine in the presence of DEAD and triphenylphosphine as described above for the preparation of compounds of formula I.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention, it is convenient to form the hydrochloride, fumarate, toluenesulfonate, hydrogen sulfate, methanesulfonate or maleate salts.

However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC).

The following examples will further illustrate the invention without, however, limiting it thereto.

All reactions were run under nitrogen and all reagents and solvents were free of water unless otherwise specified. All compounds were prepared from starting materials which are commercially available, well known in the art or for which methods of preparation are well known in the art.

EXAMPLE 1 a) 1.67 g (0.011 mol) of 3-bromo-6-ethylpyridazine was added to 1.5 mL (10 mmol) ethyl isonipecotate and 3.5 mL (20 mmol) diisopropylethylamine and 5 mL N methylpyrrolidine (NMP). This mixture was heated to 140° C. for 4 hours. Upon cooling 100 mL of water was added to the mixture and the contents were extracted with methylene chloride then washed twice with water and once with brine and the solvent evaporated in vacuo. The resulting oil was eluted through a short silica gel plug with 80% ethyl acetate and 20% hexanes and dried in vacuo. This intermediate was taken up in 25 mL THF and was exposed to 3-fold excess lithium aluminum hydride with stirring under nitrogen for 1 hour. The reaction was chilled on ice and quenched by dropwise addition of water. The slurry was dried, treated with charcoal and filtered yielding 6-ethyl-3-(4-hydroxymethyl-1-piperidinyl)pyridazine (Formula IV: $R_1=C_2H_5$; $Y=CH_2$).

b) A mixture containing 325 g of 4-cyanophenol, 346 mL of benzyl chloride and 758 g of potassium carbonate in 1.2 L of NMP was heated at 95° C. with stirring for 1.5 hrs. The reaction mixture was cooled to room temperature and poured into 5 L of cold water. The resulting white solid was collected, washed with water and hexanes and dried at 70° C. in vacuo giving 570.0 g of 4-benzyloxybenzonitrile.

A mixture of 285 g of the nitrile, 262.5 g triethylamine hydrochloride and 124 g of sodium azide in 1.5 L of DMF under nitrogen was stirred under reflux for 18 hrs. The reaction mixture was cooled to room temperature, poured into 4 L of cold water and acidified with 3N HCl. The resulting white solid was collected, washed with water and dried at 60° C. in vacuo for 48 hrs to give 337 g of 5-(4-benzyloxyphenyl)tetrazole.

To a stirred solution containing 337 g of the tetrazole and 362 mL of DIPEA in 1 L of NMP cooled to 18° C. under $N_2$ was added dropwise over 1.5 hrs 200 g of methyl iodide in 170 mL NMP. After stirring an additional hour at room temperature, the reaction mixture was diluted with 340 mL of water and the reaction mixture was diluted with 340 mL of water and cooled to 18° C. The resulting solid was collected, washed with water, recrystallized from ethanol and dried in vacuo at 50° C. to give 232.3 g of 2-methyl-5-(4-benzyloxyphenyl)-2H-tetrazole.

A mixture containing 214.2 g of the methyl tetrazole, 140 mL of concentrated hydrochloric acid and 1.08 L of glacial acetic acid was heated under reflux for 19 hrs. Most of the acetic acid was removed by evaporation under reduced pressure at 60° C. and the resulting slurry was diluted with 1.5 L of cold water. The resulting solid was collected, washed with water and dried. Recrystallization from ethanol afforded, after drying at 60° C. for 20 hrs, 104.3 g of 2-methyl-5-(4-hydroxyphenyl)-2H-tetrazole (Formula III: $R_2=R_3=H$, $R_4=CH_3$).

c) 1.57 g (6.0 mmol) of triphenylphosphine (TPP), 6.6 g (3.07 mmol) of 6-ethyl-3-(4-hydroxymethyl-1-piperdinyl)-pyridazine (Formula IV: $R_1=C_2H_5$, $Y=CH_2$) and 0.53 g (3.01 mmol) of 2-methyl-5-(4-hydroxyphenyl)-2H-tetrazole (Formula III: $R_2=R_3=$ hydrogen, $R_4=CH_3$) was dissolved in 20 ml dry methylene chloride at room temperature then chilled on ice under a nitrogen atmosphere. 0.9 mL (6 mmol) Diethyl azodicarboxylate (DEAD) was dissolved in 5 mL methylene chloride and added dropwise over 10 min to the stirred solution above. After reaction 50 mL of water was added, and the aqueous layer was extracted twice with methylene chloride. The organic layer was washed with 10% NaOH then 1N NaCl and dried over magnesium sulfate. The solution was concentrated in vacuo and the residue was acidified with 100 mL methanesulfonic acid. The yellow solution was washed 3 times with diethyl ether. The aqueous solution was treated with charcoal and filtered. The filtrate was basified with 35% NaOH. The resulting precipitate was collected, washed with water and recrystallized from methylene chloride, then methanol giving a compound of formula I ($R_1=C_2H_5$, $R_2=R_3=$hydrogen, $R_4=CH_3$, $Y=CH_2$) in 42% yield, m.p. 159°–160° C.

EXAMPLE 2

55 mmoles of 6-methyl-3-chloropyridazine was added to 75 mmoles of ethyl isonipecotate in 5 mL NMP and 20 mL diisopropylethylamine (DIPEA) and refluxed for 6 hours. The product was isolated as described in Example 1a above to give a 44% yield of 3-(4-carboethoxy-1-piperidinyl)-6-methylpyridazine. Reduction of 18.8 mmol of this compound using 56.6 mmol DIBAL in 100 mL THF with a Rochelle's salt quench gave 3-(4-hydroxymethyl-1-piperidinyl)-6-methylpyridazine (Formula IV: $R_1=CH_3$; $Y=CH_2$) which was used unpurified in the final step. Reaction of 5 mmol of the product described in Example 1b with 4.5 mmol of the 3-(4-hydroxymethyl-1-piperidinyl)-6-methyl pyridazine according to the procedure of Example 1c afforded after recrystallization from ethyl acetate at −70° C. the compound of formula I ($R_1=R_4=CH_3$, $Y=CH_2$, $R_2=R_3=$hydrogen) in 12% yield, m.p. 180°–185° C.

EXAMPLE 3

9.6 mmol of 6-n-propyl-3-chloropyridazine and 19.2 mmol of 4-hydroxypiperidine were dissolved in 2 mL NMP and 2 mL DIPEA was added dropwise. After addition the mixture was refluxed for 18 hours. The product was washed through Kieselguhr with 5% methanol/methylene chloride. Evaporation of the solvents gave a 68% yield of the 6-n-propyl-3-(4-hydroxy-1-piperidinyl)pyridazine (Formula IV, $Y=$bond, $R_1=$n-propyl).

4.5 mmol of the latter and 5 mmol of the tetrazole described in Example 1b were refluxed for 40 minutes with equimolar amounts of DEAD and TPP to give 71.9% yield (after recrystallization from ethyl acetate) of the compound of Formula I ($R_1=$n-propyl, $Y=$bond, $R_2=R_3=$hydrogen, $R_4=CH_3$), m.p. 138°–140° C.

EXAMPLE 4

2-Methyl-5-((3,5-dimethyl-4-hydroxyphenyl)-2H-tetrazole (Formula III: $R_2=R_3=R_4=CH_3$) was prepared according to the procedure of Example 1b starting with 2,6-dimethyl-4-cyanophenol. 4.5 Mmol of 6-methyl-3-(4-hydroxyl-1-piperidinyl)pyridazine (Formula IV: $R_1=$methyl, $Y=CH_2$), 1.14 g DEAD, 6.8 mmol TPP, 5 mmol of 2-methyl-5-(3,5-dimethyl-4-hydroxyphenyl)-2H-tetrazole (Formula III: $R_2=R_3=R_4=CH_3$) were reacted as described in Example 1c. Recrystallization from ethyl acetate afforded a 71.9% yield of the compound of Formula I ($R_1=R_2=R_3=R_4=$methyl, $Y=CH_2$) m.p. 183°–184° C.

EXAMPLE 5

Following a procedure similar to that of Example 3, 81 millimoles of 6-methyl-3-bromopyridazine was combined with 16 mL DIPEA and 163 mmoles of 4-hydroxypiperidine and heated to 120° for 16 hours to obtain 6-methyl-3-(4-hydroxy-1-piperdinyl)pyridazine (Formula IV: $Y=$bond, $R=CH_3$) in 24% yield. 6.8 Mmols of the latter and 7.4 mmoles of 2-methyl-5-(4-hydroxy-3,5-dimethyl phenyl)-2H-tetrazole (Formula III: $R_2=R_3=R_4=CH_3$) were reacted with equimolar amounts of DEAD and TPP essentially as described above in Example 1c. Recrystallization from methanol gave a 74% yield of the compound of Formula I ($R_1=R_2=R_3=R_4=CH_3$, $Y=$bond), m.p. 188°–189° C.

EXAMPLE 6

2.1 Mmol of the previously described 6-methyl-3-(4-hydroxy-1-piperidinyl)pyridazine (Formula IV; $R_1=CH_3$, $Y=$bond) was reacted with 9.8 mmol of previously described 2-methyl-5-(4-hydroxyphenyl)-2H-tetrazole (Formula III: $R_2=R_3=$hydrogen, $R_4=CH_3$) using TPP and DEAD according to the procedure of Example 1c. Recrystallization from ethanol gave a 67.6% yield of the compound of Formula I ($R_1=R_4=CH_3$, $R_2=R_3=$hydrogen, $Y=$bond), m.p. 157°–158° C.

EXAMPLE 7 a) 16.5 g (0.1 mol) Ethyl 4-pyridylacetate, 8.4 mL (0.1 mol) 12N hydrochloric acid and 2.5 g platinum oxide were dissolved in absolute ethanol and hydrogenated at 40 psi hydrogen on a Parr shaker. After 1 hour, the contents of the vessel were filtered and concentrated in vacuo yielding 27.79 g of ethyl 4-piperidinylacetate.

b) This sample was dissolved in 100 mL methylene chloride with 13.8 mL (0.12 mol) of benzyl chloride under nitrogen. 16.7 mL (0.12 mol) of triethylamine was added dropwise while chilling the mixture over ice. At the end of the addition the mixture came to room temperature and was stirred overnight, the organic layer was extracted with water then base, then saturated salt. The organic layer was concentrated to an oil in vacuo. Crystals formed from the oil yielding (56%) 14.61 g of ethyl N-benzyl-4-piperidinylacetate.

c) 14.40 g (0.055 mol) of this compound was taken up in 100 mL dry THF under nitrogen. 2.3 g (0.06 mol) lithium aluminum hydride was added slowly and the mixture stirred 18 hours at room temperature. The reaction was quenched with a water/diethyl ether mixture. The mixture was basified with sodium hydroxide, and the organic layer was dried over magnesium sulfate then concentrated to an oil in vacuo affording a quantitative yield of N-benzyl-4-(2-hydroxyethyl)piperidine.

d) 5.98 g (0.025 mol) of this alcohol was taken up in 125 mL of 0° C. methylene chloride. 0.025 mol of each of the following was added: triphenylphosphine, 2-methyl-5-(hydroxyphenyl)-2H-tetrazole, and dropwise diethylazodicarboxylate (in an additional 25 mL methylene chloride) under nitrogen. After this addition, the mixture was concentrated in vacuo and recrystallized from ethanol giving the intermediate

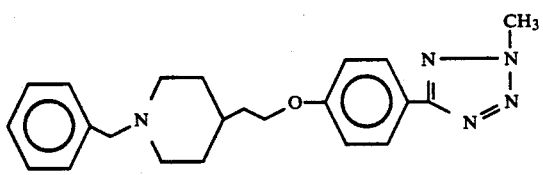

e) 3.91 g (9.64 mmol) of this intermediate, 7 mL (35 mmol) of 5M ammonium formate and a catalytic amount of palladium-on-carbon was dissolved in 50 mL of methanol and refluxed 1.5 hours. The mixture was concentrated and recrystallized from methanol yielding 1.63 g of the debenzylated product (Formula VII: $R_2=R_3=$hydrogen, $R_1=CH_3$, $Y=CH_2CH_2$).

f) 1.34 g (4.66 mmol) of this product was combined with 0.77 g (6 mmol) of 6-methyl-3-chloropyridazine with a minimum amount of NMP to permit stirring under nitrogen. The mixture was heated to 120° C. and a small amount of diisopropylethylamine added. After refluxing 8 hours the mixture was dissolved in methylene chloride, and extracted with 2N sodium hydroxide, then water, then saturated brine. The organic layer was dried over magnesium sulfate and concentrated in vacuo. The solid was recrystallized from methanol giving 0.92 g (52%) of the compound of Formula I ($R_1=R_4=CH_3$, $R_2=R_3=$hydrogen, $Y=CH_2CH_2$), m.p. 132°–133° C.

EXAMPLE 8

Following a procedure similar to that of Example 7d, 3.95 g of N-benzyl-4-(2-hydroxyethyl)piperidine and 3.45 g of the previously described 2-methyl-5-(3,5-dimethyl-4-hydroxyphenyl)-2H-tetrazole were condensed in the presence of TPP and DEAD. The resulting product was debenzylated under the conditions described in Example 7e and the debenzylated material reacted with 6-methyl-3-chloropyridazine as described in Example 7f to give the compound of Formula I ($R_1=R_2=R_3=R_4=CH_3$; $Y=CH_2CH_2$), m.p. 176°–177° C.

Biological evaluation of compounds of Formula I shows that they possess antiviral activity. They are useful in inhibiting virus replication in vitro and are primarily active against picornaviruses, including enteroviruses, echovirus and coxsackie virus, and especially numerous strains of rhinoviruses. The in vitro testing of the compounds of the invention against picornaviruses showed that viral replication was inhibited at minimum inhibitory concentrations (MIC) ranging from about 0.01 to about 5 micrograms per milliliter.

The MIC values were determined by a standard plaque reduction assay as follows: HeLa (Ohio) cells in monolayers were infected at a concentration of virus to give approximately 80 plaques per monolayer in the virus control (no drug present). The compound to be tested was serially diluted and included in the agar-medium overlay and in some cases, during the adsorption period as well. The MIC was determined to be that concentration of compound which reduced the number of plaques by 50% with respect to the untreated virus control.

In the standard test procedure, the compounds were tested against a panel of fifteen human rhinovirus (HRV) serotypes, namely HRV-2, -1A,, 1B, -6, -14, -21, -22, -15, -25, -30, -50, -67, -89, -86 and -41. The MIC value for each rhinovirus serotype was determined, and the efficacy of each compound was determined in terms of $MIC_{50}$ and $MIC_{80}$ values, which is the concentration of the compound required to inhibit 50% and 80%, respectively, of the tested serotypes.

The following Table gives the testing results with the compounds of the invention. The number of serotypes (N) is indicated after the $MIC_{80}$ figure.

TABLE

| Example No. | $MIC_{50}$ (Rhinovirus) | $MIC_{80}$ (Rhinovirus) | N = |
|---|---|---|---|
| Ex. 1 | 13.166 | 0.2815 | 15 |
| Ex. 2 | 13.337 | 0.141 | 15 |
| Ex. 3 | 15.697 | 1.823 | 13 |
| Ex. 4 | 20.137 | 1.482 | 15 |
| Ex. 5 | 0.92 | 1.8 | 2 |
| Ex. 6 | 0.27 | 0.52 | 2 |
| Ex. 7 | 6.64107 | .04 | 15 |
| Ex. 8 | 16.813 | .66 | 15 |

The antiviral compositions are formulated for use by preparing a dilute solution or suspension in a pharmaceutically acceptable aqueous, organic or aqueous organic medium for topical or parenteral administration by intravenous or intramuscular injection, or for intranasal or ophthalmic application; or are prepared in tablet, capsule, or aqueous suspension form with conventional excipients for oral administration.

What is claimed is:

1. A compound of the formula

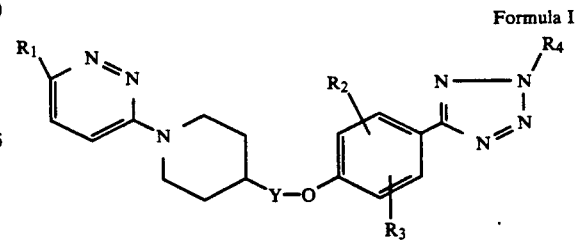

Formula I wherein
Y is a bond, or $C_1$–$C_6$ alkylene;
$R_1$ is hydrogen or $C_1$–$C_3$ lower-alkyl;
$R_2$ and $R_3$ are each independently hydrogen, $C_1$–$C_3$ lower-alkyl or halogen;
$R_4$ is hydrogen or $C_1$–$C_3$ lower-alkyl;
or a pharmaceutically acceptable acid addition salt thereof.

2. A compound according to claim 1 wherein $R_2$ and $R_3$ are independently hydrogen or methyl.

3. A compound according to claim 2 wherein $R_2$ and $R_3$ are both hydrogen or both methyl.

4. A compound according to claim 3 wherein Y is a bond, methylene or ethylene.

5. A compound according to claim 4 wherein $R_4$ is methyl.

6. A compound according to claim 5 wherein $R_1$ is methyl.

7. A compound according to claim 5 wherein $R_2$ and $R_3$ are both hydrogen.

8. A compound according to claim 7 wherein $R_1$ is ethyl.

9. A compound according to claim 8 wherein Y is methylene.

10. A compound according to claim 7 wherein $R_1$ is n-propyl.

11. A compound according to claim 10 wherein Y is a bond.

12. A composition for combating picornaviruses which comprises a pharmaceutical carrier and as an active component thereof, an effective amount of a compound of formula I

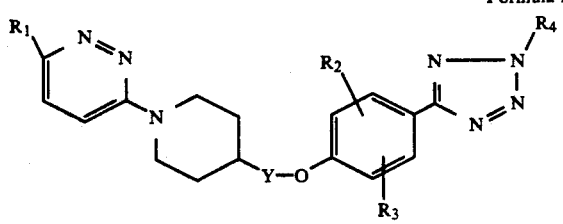

Formula I wherein
 Y is a bond, or $C_1$–$C_6$ alkylene;
 $R_1$ is hydrogen or $C_1$–$C_3$ lower-alkyl;
 $R_2$ and $R_3$ are each independently hydrogen, $C_1$–$C_3$ lower-alkyl or halogen; $R_4$ is hydrogen or $C_1$–$C_3$ lower-alkyl
or a pharmaceutically acceptable acid addition salt thereof.

13. A composition according to claim 12 wherein $R_2$ and $R_3$ are both hydrogen or both methyl.

14. A composition according to claim 13 wherein $R_4$ is methyl.

15. A composition according to claim 14 wherein $R_1$ is methyl.

16. A composition according to claim 12 wherein Y is a bond, ethylene or methylene.

17. A composition according to claim 16 wherein $R_1$ is methyl.

18. A composition according to claim 16 wherein $R_1$ is ethyl and Y is methylene.

19. A composition according to claim 16 wherein $R_1$ is n-propyl and Y is a bond.

20. A method for combating picornaviral infection which comprises administering to a patient in need of such treatment a medicament containing an effective amount of a compound of Formula I

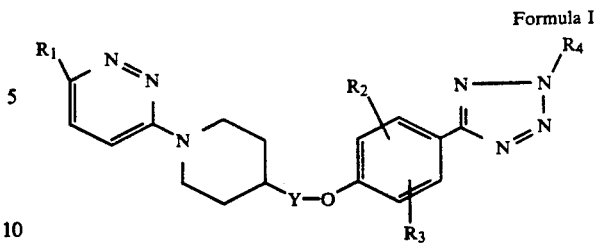

Formula I wherein
 Y is a bond, or $C_1$–$C_6$ alkylene;
 $R_1$ is hydrogen or $C_1$–$C_3$ lower-alkyl;
 $R_2$ and $R_3$ are each independently hydrogen, $C_1$–$C_3$ lower-alkyl or halogen;
 $R_4$ is hydrogen or $C_1$–$C_3$ lower-alkyl
or a pharmaceutically acceptable acid addition salt thereof.

21. A method according to claim 20 wherein $R_4$ is methyl.

22. A method according to claim 21 wherein Y is a bond, ethylene or methylene.

23. A method according to claim 22 wherein $R_2$ and $R_3$ are both methyl or both hydrogen.

24. A method according to claim 23 wherein $R_1$ is methyl.

25. A method according to claim 23 wherein $R_1$ is ethyl, Y is methylene and $R_2$ and $R_3$ are hydrogen.

26. A method according to claim 23 wherein $R_1$ is n-propyl, Y is a bond and $R_2$ and $R_3$ are hydrogen.

27. A method of combating picornaviral infection which comprises administering to a patient in need of such treatment a composition according to claim 12.

28. A method of combating picornaviral infection which comprises administering to a patient in need of such treatment a composition according to claim 17.

29. A method of combating picornaviral infection which comprises administering to a patient in need of such treatment a composition according to claim 18.

30. A method of combating picornaviral infection which comprises administering to a patient in need of such treatment a composition according to claim 19.

* * * * *